United States Patent
Cohen et al.

(10) Patent No.: US 7,642,397 B2
(45) Date of Patent: Jan. 5, 2010

(54) ABSORBENT ARTICLES COMPRISING A BODILY EXUDATE MODIFYING AGENT AND A SKIN CARE FORMULATION

(75) Inventors: Jason C. Cohen, Appleton, WI (US); David W. Koenig, Menasha, WI (US); Earl David Brock, Appleton, WI (US); Stephen A. Baratian, Roswell, GA (US); Corey Cunningham, Larsen, WI (US); Stephen Baldwin, Boise, ID (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 734 days.

(21) Appl. No.: 10/915,642

(22) Filed: Aug. 10, 2004

(65) Prior Publication Data

US 2006/0036222 A1 Feb. 16, 2006

(51) Int. Cl.
*A61F 13/47* (2006.01)
(52) U.S. Cl. ........................ 604/364; 604/359; 604/360
(58) Field of Classification Search .................. 604/364
See application file for complete search history.

(56) References Cited

U.S. PATENT DOCUMENTS

| | | | |
|---|---|---|---|
| 4,164,563 A | 8/1979 | Chang | |
| 4,357,312 A | 11/1982 | Hsieh et al. | |
| 4,514,388 A | 4/1985 | Psaledakis | |
| 4,556,560 A * | 12/1985 | Buckingham | 424/641 |
| 4,623,339 A | 11/1986 | Ciraldo et al. | |
| 4,798,603 A | 1/1989 | Meyer et al. | |
| 5,091,193 A * | 2/1992 | Enjolras et al. | 424/642 |
| 5,176,668 A | 1/1993 | Bernardin | |
| 5,176,672 A | 1/1993 | Bruemmer et al. | |
| 5,192,606 A | 3/1993 | Proxmire et al. | |
| 5,221,534 A | 6/1993 | DesLauriers et al. | |
| 5,275,589 A | 1/1994 | Bozich | |
| 5,370,876 A | 12/1994 | Noll et al. | |
| 5,436,007 A * | 7/1995 | Hartung et al. | 424/402 |
| 5,509,915 A | 4/1996 | Hanson et al. | |
| 5,558,872 A | 9/1996 | Jones et al. | |
| 5,635,191 A | 6/1997 | Roe et al. | |

(Continued)

FOREIGN PATENT DOCUMENTS

CN 1314822 A 9/2001
WO WO 99/45973 A1 9/1999

OTHER PUBLICATIONS

Hawley's Condensed Chemical Dictionary, Lewis, Sr., Richard J., pp. 46 and 937, 13th Ed. (1997).*

(Continued)

*Primary Examiner*—Tatyana Zalukaeva
*Assistant Examiner*—Paula L Craig
(74) *Attorney, Agent, or Firm*—Armstrong Teasdale LLP (57) ABSTRACT

Absorbent articles having enhanced absorption of bodily exudates are disclosed. The absorbent articles comprise a bodily exudate modifying agent and a skin care formulation. The bodily exudate modifying agent is capable of reducing the viscosity of bodily exudates such as feces and menses. The skin care formulation comprises a bodily exudate modifying agent neutralizer to neutralize the possible negative effects on skin barrier function caused by the bodily exudate modifying agents coming into direct contact with the wearer's skin.

54 Claims, 2 Drawing Sheets

U.S. PATENT DOCUMENTS

| | | | |
|---|---|---|---|
| 5,837,266 A | 11/1998 | Toma et al. | |
| 5,843,056 A | 12/1998 | Good et al. | |
| 5,855,999 A | 1/1999 | McCormack et al. | |
| 5,869,033 A | 2/1999 | Schulz | |
| 5,871,763 A * | 2/1999 | Luu et al. | 424/402 |
| 5,879,341 A | 3/1999 | Odorzynski et al. | |
| 5,998,695 A | 12/1999 | Roe et al. | |
| 6,004,307 A | 12/1999 | Colon et al. | |
| 6,004,583 A | 12/1999 | Plate et al. | |
| 6,018,093 A | 1/2000 | Roe et al. | |
| 6,149,934 A | 11/2000 | Krzysik et al. | |
| 6,340,467 B1 | 1/2002 | Morrison | |
| 6,386,778 B1 * | 5/2002 | Guay et al. | 401/45 |
| 6,395,955 B1 | 5/2002 | Roe et al. | |
| 6,433,244 B1 | 8/2002 | Roe et al. | |
| 6,464,994 B1 * | 10/2002 | Moehring | 424/402 |
| 6,503,525 B1 | 1/2003 | Paul et al. | |
| 6,503,526 B1 | 1/2003 | Krzysik et al. | |
| 6,541,629 B1 | 4/2003 | Osborne et al. | |
| 6,558,941 B2 | 5/2003 | Zuelli et al. | |
| 6,570,054 B1 | 5/2003 | Gatto et al. | |
| 6,576,810 B1 | 6/2003 | Underhill et al. | |
| 6,623,761 B2 | 9/2003 | Hassan | |
| 6,639,119 B2 | 10/2003 | Roe et al. | |
| 6,703,536 B2 | 3/2004 | Roe et al. | |
| 7,033,645 B2 * | 4/2006 | Gatto et al. | 427/374.1 |
| 7,060,867 B2 | 6/2006 | Jameson | |
| 2002/0035046 A1 | 3/2002 | Lukenbach et al. | |
| 2002/0087129 A1 | 7/2002 | Di Luccio et al. | |
| 2002/0165508 A1 | 11/2002 | Klofta et al. | |
| 2003/0026819 A1 | 2/2003 | Rios et al. | |
| 2003/0077307 A1 | 4/2003 | Klofta et al. | |
| 2004/0092901 A1 | 5/2004 | Reece et al. | |
| 2004/0247664 A1 | 12/2004 | Dreja et al. | |
| 2005/0059941 A1 | 3/2005 | Baldwin et al. | |
| 2005/0226834 A1 | 10/2005 | Lambino et al. | |
| 2005/0244480 A1 | 11/2005 | Koenig et al. | |

OTHER PUBLICATIONS

Invitation to Pay Additional Fees from PCT/US2005/019153, dated Oct. 12, 2005.

Invitation to Pay Additional Fees from PCT/US2005/019154, dated Oct. 12, 2005.

Camilli, et al., *Listeria monocytogenes*: Mutants Lacking Phosphatidylinositol-specific Phospholipase C Are Avirulent, J. Exp. Med., 1991, 173:751-754.

Mengaud, et al., Expression in *Escherichia coli* and Sequence Analysis of the Listeriolysin O Deterinant of *Listeria moncytogenes*, Infect. and Immun., 1988, 56(4):766-772.

Portnoy, et al., Capacity of Listeriolysin O, Streptolysin O, and Perfringolysin O To Mediate Growth of *Bacillus subtilis* within Mammalian Cells, Infect. and Immun., 1992, 60(7):2710-2717.

Palmer et al., Streptolysin O: A Proposed Model of Allosteric Interaction between a Pore-forming Protein and Its Target Lipid Bilayer, Biochemistry, 1998, 37(8):2378-2383.

Rossjohn et al., Structure of a Cholesterol-Binding, Thiol-Activated Cytolysin and a Model of Its Membrane Form, Cell, 1997, 89(5):685-692.

Versagel M, P, and R Overview, 2001, www.penreco.com/products/gels/gels.asp.

Versagel ME and M Series Product Bulletin, Jan. 2003, www.penreco.com/products/gels/gels.asp.

Versagel R Series Product Bulletin, Feb. 2003, www.penreco.com/products/gels/gels.asp.

Versagel Formulation Guide Product Bulletin, Jan. 2004, www.penreco.com/products/gels/gels.asp.

Protease, Protease-WIkipedia,the free encyclopedia, available at http://en.wikipedia.org/wiki/peptidase.

Protease Inhibitor (pharmacology), Protease inhibitor (pharmacology)-Wikipedia, the free encyclopedia, available at http://en.wikipedia.org/wiki/Protease_inhibitor (pharmacology).

Office action from Chinese application No. 20050086948.3, dated Dec. 26, 2008.

* cited by examiner

FIG. 2

ABSORBENT ARTICLES COMPRISING A BODILY EXUDATE MODIFYING AGENT AND A SKIN CARE FORMULATION

BACKGROUND OF INVENTION

The present invention is directed to absorbent articles such as diapers that contain a modifying agent and a skin care formulation. More particularly, the present invention is directed to absorbent articles that contain a skin care formulation and a bodily exudate modifying agent capable of reducing the viscosity of bodily exudates such as feces or menses to facilitate absorption of the exudate into the absorbent article and away from the skin. The skin care formulation comprises a bodily exudate modifying agent neutralizer, which is capable of neutralizing the modifying agent to reduce possible negative effects on skin barrier function caused by the bodily exudate modifying agents coming into direct contact with the skin of the wearer.

The stratum corneum is the outer-most layer of the skin and is responsible for regulating skin water levels and functions as a barrier against chemicals and other stress agents found in the environment. The complex arrangement of lipids in the intercellular space of the stratum corneum is responsible for the establishment of normal barrier function. Multi-layered structures of cholesterol, ceramides, and fatty acids, as well as some other minor lipids, provide the major barrier to the transport of hydrophilic substances into or through the skin. The stratum corneum is constantly exposed to physical and biological insults, which can cause a disruption in this barrier function, and numerous problems.

Absorbent articles such as diapers, training pants, incontinence products and feminine care products are worn such that they are in substantially direct contact with the stratum corneum layer of the skin of the wearer. As such, an unavoidable consequence of the use of absorbent articles is that the skin is exposed more directly to various physical and biological insults. Consequently, the barrier function of the skin covered by the absorbent article is put at risk. For example, in order to provide disposability, absorbent articles are primarily constructed of nonwoven materials. Even though nonwoven materials are engineered to have soft hand and drape, they still rub against the skin during wear causing friction. Such friction constitutes one form of physical insult to the skin barrier.

In addition to physical insults, skin covered by absorbent articles is also frequently exposed to biological insults. Biological fluids, such as urine, feces, and vaginal secretions, may contain a variety of components that can damage the skin barrier. Examples of these components include proteases, lipases, and bile acids. Once the skin barrier is compromised, these components, in addition to other constituents of biological fluids, can initiate or exacerbate inflammation of the skin. When compounded with the friction issue described above, the skin or its barrier function can be substantially damaged.

Diaper dermatitis is a type of skin condition that, in large part, originates from impaired skin barrier function. Diaper dermatitis can affect almost every infant at some point in time during the diaper wearing years. Although other factors influence the onset of diaper dermatitis, critical factors include: increased skin hydration due to the occlusion of the skin caused by diapers, enzymatic damage due to fecal and urinary enzymes, and physical damage caused by friction against the diaper surface and repeated cleaning of the skin with absorbent tissues or wet wipes.

As noted above, feces contained in the diaper can harm the skin of the wearer over time and feces leaking from the diaper almost invariably presents unpleasant, messy cleanups. Thus, several attempts have been made to add features to diapers such as barriers, pockets, spacers, transverse barriers, apertured topsheets and the like to limit the movement of fecal material across the topsheet and/or to better confine the fecal matter in the diaper. These attempts have been generally unsuccessful because they fail to address the fundamental causes of these problems (i.e., the properties of feces) and, because of their cost and complexity.

Additionally, there have been attempts to physically or chemically modify some or all of the fecal matter or other bodily exudates deposited in the article. More particularly, viscosity modifying agents such as reducing agents have been used to modify fecal matter to improve acceptance and/or retention of the exudates with the article. However, these modifying agents can also contribute to the degradation of the skin barrier function. The agents, upon contacting the skin, can disrupt the lipids of the stratum corneum layer, subjecting the skin to further irritation by the above physical and biological insults.

Based on the foregoing, it would be beneficial to provide an absorbent product that includes a bodily exudate modifying agent to allow for improved absorption of bodily exudates such as feces and menses by the absorbent product in combination with a skin care formulation that protects the skin barrier function, and improves the overall health of the skin. Additionally, it would be beneficial if the skin care formulation included a bodily exudate modifying agent neutralizer to neutralize the modifying agent and reduce the possible negative effects on skin caused by the bodily exudate modifying agent contacting the skin.

SUMMARY OF THE INVENTION

The present invention is directed to absorbent articles comprising a bodily exudate modifying agent and a skin care formulation. The bodily exudate modifying agent is capable of reducing the viscosity of feces, menses, or other bodily exudates allowing for enhanced absorption of these exudates into the absorbent article and away from the surface of the skin. The skin care formulation, which is transferred to the skin of the wearer during use of the product, comprises a bodily exudate modifying agent neutralizer, which is capable of protecting the skin from possible negative effects caused by the bodily exudate modifying agents coming into direct contact with the skin. The skin care formulation may additionally comprise other additives to improve skin health.

Therefore, the present invention is directed to an absorbent article comprising an absorbent body, a bodyside liner, a bodily exudate modifying agent, and a skin care formulation. The bodily exudate modifying agent is capable of reducing the viscosity of bodily exudates upon contact therewith. The skin care formulation comprises a bodily exudate modifying agent neutralizer, which neutralizes the modifying agent upon contact to reduce potential damage to the skin.

The present invention is further directed to an absorbent article comprising an absorbent body, a bodyside liner, microencapsulated water, a bodily exudate modifying agent, and a skin care formulation. The bodily exudate modifying agent is capable of reducing the viscosity of bodily exudates. The skin care formulation comprises a bodily exudate modifying agent neutralizer.

The present invention is further directed to a method for reducing the viscosity of a bodily exudate in an absorbent article. The method comprises: (i) providing an absorbent article having a bodyside liner and an absorbent body, wherein the bodyside liner comprises an encapsulated bodily exudate modifying agent and a skin care formulation; (ii) contacting a bodily exudate with the bodyside liner to provide for direct contact between the encapsulated bodily exudate modifying agent and the bodily exudate. The bodily exudate modifying agent is capable of reducing the viscosity of bodily exudates upon contact therewith. The skin care formulation comprising a bodily exudate modifying agent neutralizer.

DETAILED DESCRIPTION OF THE PRESENTLY PREFERRED EMBODIMENTS

In accordance with the present invention, it has been discovered that absorbent articles comprising a viscosity modifying agent and a skin care formulation comprising a modifying agent neutralizer have numerous desirable properties. The viscosity modifying agents can be used to modify bodily exudates, such as feces and menses, in the absorbent article to provide for quicker, cleaner removal and storage of these exudates away from the skin of the wearer. The bodily exudate modifying agent is capable of reducing the viscosity of feces, menses, or other bodily exudates to allow for improved flow and absorption of these exudates into the absorbent body of the absorbent article and away from the skin. The skin care formulation present in or on the absorbent article is transferred to the skin and provides for enhanced barrier function to protect the skin from biological insults and neutralizes the potential negative effects of the bodily exudate modifying agent if it comes into contact with the skin. The present invention provides the wearer with cleaner and healthier skin.

The present invention can suitably be used to provide a benefit to any skin type, for example, labial skin, glabrous skin, and hairy skin.

The present invention is primarily described herein in combination with an absorbent disposable diaper. It is readily apparent to one skilled in the art based on the disclosure herein, however, that the modifying agents and the skin care formulations described herein can also be used in combination with numerous other disposable absorbent articles such as, for example, training pants, adult incontinence garments, feminine napkins, and the like.

Figure 1:
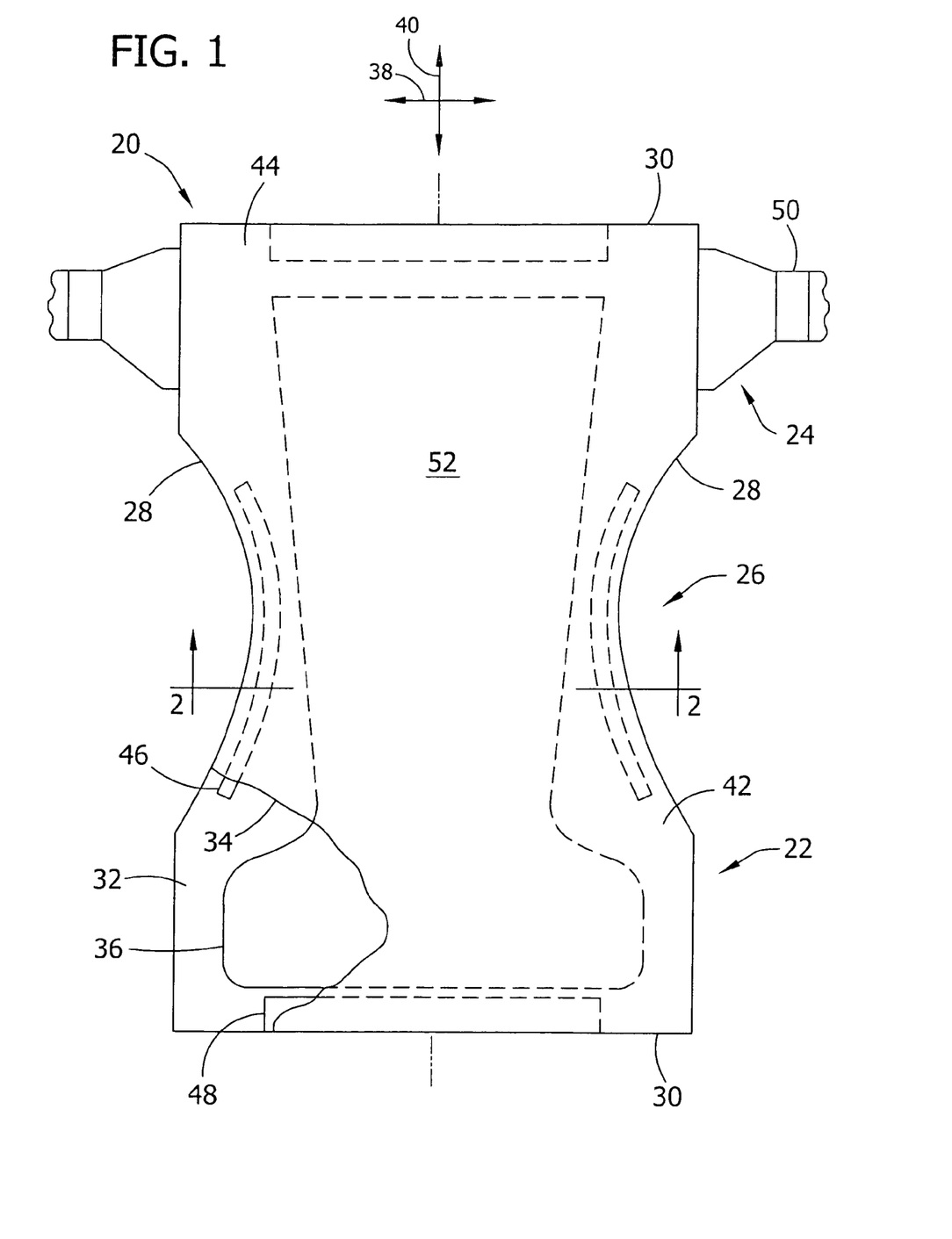
FIG. 1 representatively shows a partially cut away top plan view of an absorbent article in a stretched and laid flat condition with the surface of the article which contacts the skin of the wearer facing the viewer.
Figure 2:
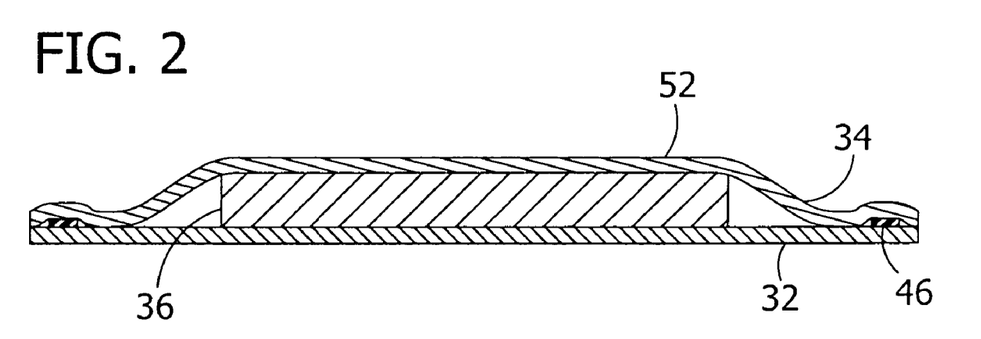
FIG. 2 representatively shows a sectional view of the absorbent article of FIG. 1 taken along line 2-2.

With reference to FIGS. 1 and 2, an integral absorbent article, such as a disposable diaper 20, generally defines a front waist section 22, a rear waist section 24, an intermediate section 26 which interconnects the front and rear waist section, a pair of laterally opposed side edges 28, and a pair of longitudinally opposed end edges 30. The front and rear waist sections include the general portions of the article which are constructed to extend substantially over the wearer's front and rear abdominal regions, respectively, during use. The intermediate section of the article includes the general portion of the article, which is constructed to extend through the wearer's crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

FIG. 1 is a representative plan view of the diaper 20 in a flat, non-contracted state. Portions of the structure are partially cut away to more clearly show the interior construction of the diaper 20, and the surface of the diaper which contacts the wearer is facing the viewer. The diaper 20 includes a substantially liquid impermeable outer cover 32, a porous, liquid permeable bodyside liner 34 positioned in facing relation with the outer cover 32, and an absorbent body 36, such as an absorbent pad, which is located between the outer cover and the bodyside liner. The diaper 20 also defines a lateral direction 38 and a longitudinal direction 40. Marginal portions of the diaper 20, such as marginal sections of the outer cover 32, may extend past the terminal edges of the absorbent body 36. In the illustrated embodiment, for example, the outer cover 32 extends outwardly beyond the terminal marginal edges of the absorbent body 36 to form side margins 42 and end margins 44 of the diaper 20. The bodyside liner 34 is generally coextensive with the outer cover 32, but may optionally cover an area which is larger or smaller than the area of the outer cover 32, as desired.

To provide improved fit and to help reduce leakage of body exudates from the diaper 20, the side margins 42 and end margins 44 of the diaper may be elasticized with suitable elastic members, such as leg elastic members 46 and waist elastic members 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 48 can be employed to elasticize the end margins 44 of the diaper 20 to provide elasticized waistbands. The waist elastics are configured to operably gather and shirr the waistband sections to provide a resilient, comfortably close fit around the waist of the wearer.

The elastic members 46 and 48 are secured to the diaper 20 in an elastically contractible condition so that in a normal under strain configuration, the elastic members effectively contract against the diaper 20. For example, the elastic members 46 and 48 may be elongated and secured to the diaper 20 while the diaper is in an uncontracted condition. In FIGS. 1 and 2, the elastic members 46 and 48 are illustrated in their uncontracted, stretched condition for the purpose of clarity. The diaper 20 may also include a pair of elasticized, longitudinally extending containment flaps (not shown), which are configured to maintain an upright, perpendicular arrangement in at least the intermediate section 26 of the diaper 20 to serve as an additional barrier to the lateral flow of body exudates. Suitable constructions and arrangements of containment flaps are well known to those skilled in the art.

Alternatively, the diaper 20 may include a pair of separate, elasticized and gathered leg gussets (not shown) or combination leg gussets/containment flaps (not shown) which are attached to the diaper along the side margins 42 in at least the intermediate section 26 of the diaper 20 to provide elasticized leg cuffs. Such gussets or combination gussets/containment flaps may be configured to extend beyond and bridge across the respective concave portion of the side margins 42.

The diaper 20, as representatively illustrated in FIGS. 1 and 2, may further include a pair of fasteners 50 employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member can be associated with each fastener and may be constructed to be nonelasticized, or to be elastically stretchable at least along the lateral direction 38 of diaper 20.

The diaper may further include a surge management layer (not shown) positioned between the bodyside liner 34 and the absorbent body 36 which is configured to efficiently hold and distribute liquid exudates to the absorbent body 36. The surge management layer can prevent the liquid exudates from pooling and collecting on the portion of the diaper positioned against the wearer's skin, thereby reducing the level of skin hydration. Suitable constructions and arrangements of surge management layers are well known to those skilled in the art. Other suitable diaper components may also be incorporated on absorbent articles described herein.

The diaper 20 may be of various suitable shapes. For example, the diaper may have an overall rectangular shape, T-shape, or an approximately hour-glass shape. In the shown embodiment, the diaper 20 is I-shaped. Examples of diaper configurations suitable for use in connection with the instant application and other diaper components suitable for use on diaper 20 are described in U.S. Pat. No. 4,798,603 issued Jan. 17, 1989 to Meyer et al.; U.S. Pat. No. 5,176,668 issued Jan. 5, 1993, to Bernardin; U.S. Pat. No. 5,176,672 issued Jan. 5, 1993 to Bruemmer et al.; U.S. Pat. No. 5,192,606 issued Mar. 9, 1993 to Proxmire et al.; and U.S. Pat. No. 5,509,915 issued Apr. 23, 1996 to Hanson et al., the disclosures of which are hereby incorporated by reference. The various aspects and configurations of the invention can provide distinctive combinations of softness, body conformity, reduced red-marking of the wearer's skin, reduced hydration, and improved containment of body exudates.

The various components of the diaper 20 are integrally assembled together employing various types of suitable attachment means, such as adhesive, sonic bonds, thermal bonds, or combinations thereof. In the shown embodiment, for example, the bodyside liner 34 and the outer cover 32 are assembled to each other and to the absorbent body 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 46 and 48 and the fasteners 50, may be assembled into the diaper 20 by employing the above-identified attachment mechanisms.

The outer cover 32 of the diaper 20, as representatively illustrated in FIGS. 1 and 2, may suitably be composed of material which is either liquid permeable or liquid impermeable. It is generally preferred that the outer cover 32 be formed from a material which is substantially impermeable to liquids. For example, a typical outer cover can be manufactured from a thin plastic film or other flexible liquid-impermeable material. For example, the outer cover 32 may be formed from a polyethylene film having a thickness of from about 0.012 millimeter (0.5 mil) to about 0.051 millimeter (2.0 mils). If it is desired to present the outer cover with a more clothlike feeling, the outer cover 32 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mils) may have thermally laminated thereto a spunbond web of polypropylene fibers, which fibers have a denier of about 1.5 to 2.5 per filament, which nonwoven web has a basis weight of about 17 grams per square meter (0.5 ounce per square yard). Methods of forming such clothlike outer covers are known to those skilled in the art. Further, the outer cover 32 may be formed of a woven or nonwoven fibrous web layer which has been totally or partially constructed or treated to impart a desired level of liquid impermeability to selected regions that are adjacent or proximate to the absorbent body 36.

Desirably, the outer cover 32 may be composed of a "breathable" material which permits vapors to escape from the absorbent body 36 while still preventing liquid exudates from passing through the outer cover 32. For example, the outer cover 20 is desirably constructed to be permeable to at least water vapor and has a water vapor transmission rate of at least about 1000 $g/m^2/24$ hours, desirably at least about 1500 $g/m^2/24$ hours, more desirably at least about 2000 $g/m^2/24$ hours, and even more desirably at least about 3000 $g/m^2/24$ hours. Materials which have a water vapor transmission rate less than those above do not allow a sufficient amount of air exchange and undesirably result in increased levels of skin hydration. As used herein, the phrase "water vapor transmission rate" (WVTR) refers to the WVTR value according to the Water Vapor Transmission Rate Test which is described in further detail herein below.

In a particular embodiment, the outer cover 20 is provided by a microporous film/nonwoven laminate material comprising a spunbond nonwoven material laminated to a microporous film. For example, the laminate may include a 0.6 osy (20.4 gsm) polypropylene spunbond material thermally attached to a 18.7 gsm stretched microporous film. The film may include from about 20 percent to about 75 percent by weight calcium carbonate particulates and the remainder primarily low density polyethylene. The film is then stretched which causes the polyethylene component to stretch while the particulates remain unstretched, thus causing voids to develop around the calcium carbonate particles in the film. The resulting laminate may define a water vapor transmission rate of from about 1000 to about 5000 $g/m^2/24$ hours or more.

Examples of suitable breathable materials for the outer cover 20 are also described in U.S. Pat. No. 5,879,341 issued Mar. 9, 1999 to Odorzynski et al. and entitled "ABSORBENT ARTICLE HAVING A BREATHABILITY GRADIENT"; U.S. Pat. No. 5,843,056 issued Dec. 1, 1988, to Good et al. and entitled ABSORBENT ARTICLE HAVING A COMPOSITE BREATHABLE OUTER COVER"; and U.S. Pat. No. 5,855,999 issued Jan. 5, 1999 to McCormack et al. and entitled "BREATHABLE, CLOTH-LIKE FILM/NONWOVEN COMPOSITE", the disclosures of which are herein incorporated by reference.

The absorbent body 36 of the diaper 20, as representatively illustrated in FIGS. 1 and 2, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va., and DOW DRYTECH 2035LD polymer available from Dow Chemical Company located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on a total weight of the absorbent body 36.

Optionally, a substantially hydrophilic tissue wrapsheet (not shown) may be employed to help maintain the integrity of the airlaid fibrous structure of the absorbent body 36. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer, which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass.

The bodyside liner 34, as representatively illustrated in FIGS. 1 and 2, suitably presents a bodyfacing surface which is compliant, soft feeling, and non-irritating to the wearer's skin. Further, the bodyside liner 34 may be less hydrophilic than the absorbent body 36, to present a relatively dry surface to the wearer, and may be sufficiently porous to be liquid permeable, permitting liquid to readily penetrate through its thickness. A suitable bodyside liner 34 may be manufactured from a wide selection of web materials, such as porous foams, reticulated foams, apertured plastic films, natural fibers (i.e., wood or cotton fibers), synthetic fibers (i.e., polyester or polypropylene fibers), or a combination of natural and synthetic fibers. The bodyside liner 34 is suitably employed to help isolate the wearer's skin from liquids held in the absorbent body 36.

Various woven and nonwoven fabrics can be used for the bodyside liner 34. For example, the bodyside liner 34 may be composed of a meltblown or spunbonded web of polyolefin fibers. The bodyside liner 34 may also be a bonded-carded web composed of natural and/or synthetic fibers. The bodyside liner 34 may be composed of a substantially hydrophobic material, and the hydrophobic material may, optionally, be treated with a surfactant, a wetting agent, or otherwise processed to impart a desired level of wettability and hydrophilicity.

In a particular embodiment, the bodyside liner 34 comprises a nonwoven, spunbond, polypropylene fabric composed of about 1-3 denier fibers formed into a web having a basis weight of about 20 grams per square meter and a density of about 0.13 gram per cubic centimeter. The fabric may be surface treated with about 0.3 weight percent of a surfactant mixture, which contains a mixture of AHCOVEL Base N-62 and GLUCOPOAN 220UP surfactant in a 3:1 ratio based on a total weight of the surfactant mixture. The AHCOVEL Base N-62 is purchased from Uniqema (New Castle, Del.) and includes a blend of hydrogenated ethoxylated castor oil and sorbitan monooleate in a 55:45 weight ratio. The GLUCOPON 220UP is purchased from Cognis Corporation and includes alkyl polyglycoside. The surfactant may be applied by any conventional means, such as spraying, printing, brush coating, or the like. The surfactant may be applied to the entire bodyside liner 34, or may be selectively applied to particular sections of the bodyside liner 34, such as the medial section along the longitudinal centerline of the diaper, to provide greater wettability of such sections.

As discussed above, the absorbent articles of the present invention include a bodily exudate modifying agent and a skin care formulation. As used herein, the term "bodily exudate" means secretions from the human body that have a viscosity greater than that of urine. Bodily exudates include, for example, solid, semi-solid and liquid bowel movements, menses, and other vaginal and anal secretions. Suitably, the bodily exudate modifying agents are capable of reducing the viscosity of bodily exudates, such as feces or menses, upon contact therewith. By reducing the viscosity of the exudates, there may be improved absorption of the exudates into the absorbent body of the absorbent article and away from the skin of the wearer. This results in improved skin health as numerous compounds contained in the bodily exudates that could damage the skin upon contact therewith are substantially removed from the area of the disposable absorbent product in contact with the surface of the skin. The bodily exudate modifying agents described herein can be used alone or in combination.

As used herein, the term "bodily exudate modifying agent" refers to a chemical composition capable of reducing the viscosity of bodily exudates, such as feces and menses, through chemical modification to allow for enhanced absorption of the bodily exudates by one or more areas of the absorbent article. As such, these bodily exudate modifying agents may be used to enhance the ease of bodily exudate penetration into an absorbent article and away from the skin. Suitably, the bodily exudate modifying agent reduces the viscosity of at least some of the bodily exudate by at least about 5%, more suitably, at least about 25%. Such a reduction in viscosity results in the exudates flowing much more easily into the desired area of the absorbent article, which may be, for example, the absorbent body.

Typically, the bodily exudate modifying agent is present in the absorbent article in an amount of from about 0.01% (by weight of the article) to about 10% (by weight of the article). More suitably, the bodily exudate modifying agent is present in the absorbent article in an amount of from about 0.1% (by weight of the article) to about 0.5% (by weight of the article). Based on the disclosure herein, one skilled in the art will recognize that the exact amount of modifying agent required to provide the intended function may vary depending upon the desired application, and the exact location of the modifying agent in the absorbent article.

The location of the bodily exudate modifying agent within the absorbent article is not critical, and it may be introduced into or onto the absorbent article in any suitable location to allow contact with the exudate. The modifying agent maybe introduced into two or more areas of the absorbent article in some embodiments to allow for increased activity. In one specific embodiment, the bodily exudate modifying agent is introduced into the absorbent body of the absorbent article. The modifying agent can be introduced only into a specified area of the absorbent body, or may be distributed evenly or unevenly throughout the entire absorbent body. Also, the modifying agent could be introduced onto any superabsorbent material present in the absorbent body.

Where the modifying agent is introduced into the absorbent body, upon defecation and/or urination, the modifying agent is contacted with fluid and is drawn through the absorbent body and bodyside liner where it contacts the bodily exudate and begins to reduce the viscosity of the exudate to facilitate absorption of the exudate into the absorbent body. In this embodiment, a substantial amount of the modifying agent present in the absorbent body will contact the exudate as opposed to the skin as the exudate is located between the modifying agent and the skin. As such, there is a reduced likelihood of direct skin contact by the modifying agent.

In another embodiment, the bodily exudate modifying agent is introduced onto the outward facing surface of the bodyside liner; that is, the modifying agent is introduced onto the side of the bodyside liner that faces away from the wearer. In this embodiment, upon defecation and/or urination, the modifying agent is contacted by fluid and is drawn through the thin bodyside liner and contacted with the exudate where it reduces the viscosity of the exudate. With this embodiment, it maybe possible to utilize a reduced amount of modifying agent as the agent need only move through the liner to contact the exudate, and is not required to move through the absorbent body.

In another embodiment, the bodily exudate modifying agent is introduced onto the bodyfacing surface of the bodyside liner such that, upon being contacted with feces, it immediately begins to reduce the viscosity of the feces to improve absorption of the feces into the absorbent body of the product. This embodiment provides for the quickest reduction in viscosity of the feces, as the modifying agent is not required to travel through one or more layers of the absorbent article to reach the feces. In this embodiment, it is generally preferred, although not required, that the bodily exudate modifying agent be first encapsulated prior to introducing it onto the bodyside liner to reduce the likelihood of the modifying agent contacting the skin of the wearer prior to the introduction of feces into the absorbent article. By encapsulating the modifying agent, it can be held away from the skin until feces is present and causes the capsules to dissolve or disintegrate and release the modifying agent.

The modifying agent maybe microencapsulated in a shell-type material that will dissolve, disintegrate, rupture, or otherwise breakdown upon contact with urine and/or feces to allow for the release of the modifying agent. Suitable microencapsulated shell materials are known in the art and include cellulose-based polymeric materials (e.g., ethyl cellulose), lactic acid-based aliphatic polyesters, carbohydrate-based materials (e.g., cationic starches and sugars) and materials derived therefrom (e.g., dextrins and cyclodextrins) as well as other materials compatible with human tissues.

As will be recognized by one skilled in the art based on the disclosure herein, the modifying agent may first be encapsulated prior to introduction into any area of the absorbent article to reduce the potential for the modifying agent to contact the skin.

Other suitable locations of the bodily exudate modifying agent can include, for example, surge layers, leg elastic members, and waist elastic members of the absorbent article.

In one embodiment, the bodily exudate modifying agent is an enzyme capable of interacting with the bodily exudate and reducing its viscosity. Enzymes are complex proteins that are produced by cells and act as catalysts in biochemical reactions. More particularly, specific enzymes can be utilized in the present invention to reduce the viscosity of bodily exudates. Suitable enzymes for use as bodily exudate modifying agents in the absorbent articles as described herein include amylase, lysozyme, zymolyase, celulase, protease, lipase, urease, elastase, carbohydrase, cathepsin G, myeloperoxidase, cytolysins, such as phospholipase and listeriolysin, streptolysin, perfringolysin, and combinations thereof. Suitable proteases include serine proteases, cysteine proteases, and metalloproteases. These enzymes catalyze reactions on the surface of the exudate that result in a breakdown of the exudate and a decreased viscosity of the exudate.

In another embodiment, the bodily exudate modifying agent is a reducing agent. For example, agents that reduce disulfide bonds (—S—S-bonds), as found in colonic mucous (colonic mucous generally comprises various macromolecular glycoproteins linked by disulfide bonds), can effect a significant viscosity reduction in feces having high mucous content, such as runny feces. This reduction of disulfide bonds denatures the various glycoproteins. Without being bound to a particular theory, it is believed that the denaturing of the proteins by the reduction of the mucin disulfide bonds (which function as crosslinks between mucin polymer chains) significantly reduces the average molecular weight of the glycoprotein structure in feces, such as runny feces, to a level well below the "gel point" of the mucin (i.e., long-distance structure becomes impossible due to the relatively small size of the glycoproteins). This reduction in average molecular weight results in a decrease in viscosity.

Suitable reducing agents can include sulfites such as sodium hydrogensulphite, sodium sulfite and sodium dithionite, thiols, thiol alcohols (e.g., 2-mercaptoethanol, dithiothreitol, and dithioerythritol), mercaptoacetic acid, sodium thioglycolate, thiolactic acid, thioglycoamide, glycerol monothioglycolate, borohydrides (e.g., sodium borohydride), ternary amines, thiocyanates such as sodium thiocyanate, thiosulfates such as sodium thiosulfate, cyanides such as sodium cyanide, thiophosphates such as sodium thiophosphate, arsenites such as sodium arsenite, phosphines such as triphenyl phosphine, phenols such as thiophenol and p-nitrophenol, betaines, lithium aluminum hydride, guanidine hydrochloride, stannous chloride, hydroxylamine, LiHB($C_2H_5$)$_3$, zinc metal, Raney nickel, hydrazines, and substituted hydrazines. Two or more of the reducing agents can also be used in combination to reduce the viscosity of the exudate.

Other suitable reducing agents include stabilized radicals. Examples of stabilized radicals that can act as reducing agents include alkyl tin hydrides, such as tributyl tin hydride, organic peroxides, such as benzoyl peroxide and di-tert-butyl peroxide, azobisisobutyronitrile (AIBN), and triphenyl carbenium salts.

In another embodiment, the bodily exudate modifying agents are agents that can activate enzymatic autolysins, such as peptidoglycan hydrolases, in the bacteria present in bodily exudates. These activated autolysins will catalyze the lysis of the bacterial cell wall through the use of the cell's own enzymes. As the bacterial cell wall is destroyed, water is liberated from inside the bacterial cell. This released water from inside of the cell produces a dilution effect around the exudate, which results in the reduction of the viscosity of the bodily exudate.

One suitable example of a bodily exudate modifying agent that can activate autolysins in bacteria found in exudate is a metal-based modifying agent. As used herein, the term "metal-based modifying agent" refers to any chemical compound containing a metal capable of activating an autolysin, which can reduce the viscosity of bodily exudates. In one embodiment, the metal-based modifying agents include, but are not limited to, magnesium-based modifying agents, barium-based modifying agents, calcium-based modifying agents, and combinations thereof.

Suitable magnesium-based modifying agents are magnesium oxide, magnesium hydroxide, and magnesium chloride. Suitable barium-based modifying agents are barium oxide, barium hydroxide, and barium chloride.

Specifically, calcium-based modifying agents are required for activating calpain-type protease autolysins. Some suitable calcium-based modifying agents useful for the present invention can include calcium oxide, calcium hydroxide, calcium chloride, and calcium carbonate.

The metal-based modifying agents can also suitably be metal salts. Suitably, the metal salt can be selected from the group consisting of iron salts, aluminum salts, calcium salts, and combinations thereof.

Additionally, various peptides can be used to activate autolysins in bacteria and reduce the viscosity of the exudate. Suitably peptides for use in the present invention are cationic peptides. Cationic peptides cause a deregulation of the anionic and amphiphilic regulators of the autolytic wall components, such as enzymes (muramidases), lipoteichoic acid, and Forssman antigens. This deregulation results in hydrolysis of the peptidoglycan found in the normal bacteria cell wall, bacteriolysis, and cell death. For example, a suitable cationic peptide is niacin.

Some pore-forming toxins can further induce autolysins. These toxins shut down transport channels in bacterial cell walls, forcing the channels to remain open. As such, water is released into the absorbent article from inside the bacterial cell. As stated above, this produces a dilution effect, which reduces the viscosity of bodily exudates. Suitably pore-forming toxins include alpha-toxins, cytolysin A, and seticholysins.

In addition to agents that can activate autolysins, certain nanoemulsions, alternatively known as nanoparticles, can cause lysis of bacterial cell walls. The bacterial cell wall ruptures when the walls come into contact with the nanoemulsions. As stated above, this results in the release of water from inside the bacterial cell, causing a dilution effect, which reduces the viscosity of the bodily exudates.

Methods for preparing nanoemulsions or nanoparticles suitable for use in the present invention are well known and disclosed, for example, in U.S. Pat. Nos. 6,558,941 and 6,623,761. For example, in one embodiment, nanoemulsions can be prepared through the process of wet grinding. Wet grinding involves the mechanical crushing of brittle particles, using hard beads made of glass, porcelain, zirconium oxide, or similar materials of about 1-2 mm in diameter, and aqueous solution of a hydrophilic material. The hydrophilic solution, which can be a surface active agent, surface modifier, or surface stabilizer, prevents aggregation or caking of the ground particles.

Another suitable method is the liquid antisolvent technique, which involves dissolving a water insoluble compound in a suitable organic solvent, and diluting that solution with a non-solvent. The non-solvent is miscible in the solution. The non-solvent neither dissolves the compound nor causes its precipitation from the original solvent. Solid nanoparticles are then generated by carefully controlling the precipitation step by addition of an antisolvent liquid, such as water or an aqueous solution. Since the formation of the nanoparticles is solely dependent on the diffusion of totally miscible liquids under non-structural geometry, or boundaries, resultant particle size, surface, and shape are critically sensitive to minimal changes in the precipitation conditions.

One embodiment suitable for the present invention includes nanoemulsions composed of oil particles, the surfaces of which are occupied by an amphoteric emulsifier in aqueous dispersions. These oil particles are of a diameter of less than about 100 nm, and more suitably, of less than 40 nm. Other suitable nanoemulsions for use in the present invention may include vegetable oil in water emulsions, triglycerides in water emulsions, fatty acid esters in water emulsions, and combinations thereof.

In another embodiment, surfactants, and specifically mild-type surfactants, can be used as bodily exudate modifying agents. Surfactants lower the surface tension of liquids, and as such, the use of mild surfactants in the present invention will facilitate the release of moisture, thus enhancing the breakdown of the bodily exudates. Mild surfactants are typically preferred to reduce the likelihood of the surfactant damaging the skin. Suitable mild surfactants include sodium mono lauryl phosphate, potassium mono lauryl phosphate, diethanolamine mono lauryl phosphate, triethanolamine mono lauryl phosphate, sodium mono coco phosphate, potassium mono coco phosphate, triethanolamine mono coco phosphate, sodium mono capric phosphate, potassium mono capric phosphate, triethanolamine mono capric phosphate, nonionic surfactants, such as PLURONIC surfactants, and combinations thereof.

While the use of the above discussed bodily exudate modifying agents will generally result in a reduced viscosity of the bodily exudate upon contact therewith in the absorbent article, some of the bodily exudate modifying agents, such as lipase and protease enzymes, may cause an irritation on the skin surface that is uncomfortable and can predispose the skin to infection by microorganisms if they remain in contact with the skin for any appreciable period of time. As such, the absorbent articles of the present invention further include a skin care formulation. This formulation, upon transfer to the skin, can improve the skin barrier function and, additionally, neutralize the modifying agents that may cause skin problems upon contact therewith; that is, the skin care formulation may form a barrier layer in the skin to keep unwanted agents away from the skin.

Although the skin care formulation can be applied to any suitable area of the absorbent article, the skin care formulation is preferably applied to the bodyfacing side of the bodyside liner of the absorbent article such that, upon wear by a user, the skin care formulation can be substantially transferred from the bodyside liner to the surface of the skin. Upon transfer from the bodyside liner to the skin, the skin care formulation can form a protective barrier layer on the skin surface to keep potentially harmful substances away from the skin and improve overall skin health in the diaper area. Additionally, in some embodiments, the skin care formulation can neutralize any exudate modifying agents that contact the skin.

The skin care formulation is present in the absorbent articles of the present invention in an amount of from about 0.01% (by weight of the article) to about 10% (by weight of the article). More suitably, the skin care formulation is present in the absorbent articles of the present invention in an amount of from about 0.1% (by weight of the article) to about 0.5% (by weight of the article).

The skin care formulation for application to the absorbent article typically comprises a bodily exudate modifying agent neutralizer. As used herein, the term "bodily exudate modifying agent neutralizer" includes any chemical compound that can chemically neutralize or inhibit the effect of the bodily exudate modifying agents and reduce their potentially harmful effects on the skin surface.

The skin care formulations to be applied to the absorbent articles of the present invention include a bodily exudate modifying agent neutralizer in an amount of from about 0.01% (by weight of the formulation) to about 10% (by weight of the formulation). More suitably, the skin care formulations to be applied to the absorbent articles of the present invention include bodily exudate modifying agent neutralizers in an amount of from about 0.1% (by weight of the formulation) to about 0.5% (by weight of the formulation).

In one embodiment, the bodily exudate modifying agent neutralizer is an enzyme inhibitor. Inhibitors of enzyme activity are well known and are typically classified as competitive inhibitors, which compete with the substrate for binding at the active site on the enzyme, and non-competitive inhibitors, which bind to a site other than the active site to inactivate the enzyme. Suitably, enzyme inhibitors useful in the skin care formulations described herein include protease inhibitors, lipase inhibitors, elastase inhibitors, urease inhibitors, amylase inhibitors, and combinations thereof. More suitably, the enzyme inhibitors are selected from the group consisting of soybean trypsin inhibitor, lima bean protease inhibitor, corn protease inhibitor, Bowman-Birk inhibitor, pancreatic trypsin inhibitor, ovomucoids, chymostatin, leupeptin and its analogs, bestatin and its analogs, antipain, antithrombin III, hirudin, cystatin, $\alpha_2$-macroglobulin, $\alpha_1$-antitrypsin, pepstatin and its analogs, TLCK, TPCK, tranexamic acid and its salts, glycyrrhizic acid and its salts, stearylglycyrrhetinate, 18-β-glycyrrhetinic acid and its salts, colloidal oat extracts, elhibin, 4-(2-aminoethyl)-benzenesulfonylfluoride HCl, quercetin, phytic acid and its salts, ethylenediamine tetraacetic acid (EDTA) and its salts, hexamidine and its salts, pentamidine and its salts, benzamidine and its salts and derivatives, p-aminobenzamidine and its salts and derivatives, guanidinobenzoic acid and its salts and derivatives, alkyl hydroxamic acid and its salts and derivatives, phosporamidate and its derivatives, water soluble salts of metals, zinc salts of both saturated and unsaturated monocarboxylic acids, glycerol triesters of fatty acids, block copolymers of propylene oxide and ethylene oxide, chlorhexidine, cholestyramine, acarbose, voglibose, miglitol, emiglitate, camiglibose, pradimicin Q, salbostatin, tendamistat, trestatins, inhibitors derived from plants, such as from wheat, rice, maize, barley, and other cereal grains, beans, and seaweed, tetrahydrolipstatin, lipstatin, valilactone, esterastin, ebelactone A and B, 1,6-di(O-(carbamoyl)cyclohexanone oxime)hexane, and combinations thereof.

In another embodiment, the bodily exudate modifying agent neutralizer is a skin irritant sequestering agent. As used herein, the term "sequestering agent" means a material that can adsorb a target molecule, such as a fecal protease, by covalent or non-covalent mechanisms. In certain preferred embodiments, the affinity for the irritant is high, rapid, and irreversible. Adsorption of the irritant to the sequestering agent should preclude or significantly diminish the ability of a target irritant to penetrate into, and potentially through, the stratum corneum. As used herein, the term "sequestration" is defined as the process of binding of an irritant to a sequestering agent, by covalent or non-covalent mechanisms.

The adsorption of these target molecules, i.e., the bodily exudate modifying agents, minimizes their ability to penetrate into the skin and cause skin irritation. Suitable skin irritant sequestering agents can include clays. Particularly, the clay is suitably selected from the group consisting of bentonite, laponite, montmorillonite, beidelite, hectorite, saponite, stevensite, and combinations thereof. Also suitable as sequestering agents are silica, titanium dioxide, hydroxyapatite, alumina, ion-exchange resin, and combinations thereof.

In another embodiment, the bodily exudate modifying agent neutralizer is an oxidizing agent. In a reduction-oxidation reaction, the oxidizing agent oxidizes or extracts electrons from the reducing agent. As such, the effects of bodily exudate modifying agents like reducing agents will be neutralized by the oxidizing agent. Suitable oxidizing agents are citric acid, malic acid, alphahydroxy acid, hydrogen peroxide, and peroxide.

In another embodiment, the bodily exudate modifying agent neutralizer is a binding protein. A binding protein, like the enzyme inhibitors discussed above, will bind to an active or inactive site on the bodily exudate modifying agent, inhibiting the action of the bodily exudate modifying agent. Suitable binding proteins for the present invention include serum albumin, histone proteins, plant proteins, animal proteins, fish proteins, yeast extract, algal proteins, and bacterial proteins.

In another embodiment, the bodily exudate modifying agent neutralizer is a zwitterion. Zwitterions, which carry both a negative and a positive charge, can act as an acid or base. As such, zwitterions for the use in the present invention can neutralize the bodily exudate modifying agents discussed above, particularly when the agents are mild surfactants, by neutralizing the charge of the modifying agent. Suitable zwitterions include, for example, amino acids such as alanine and betaine glycine.

In addition to the bodily exudate modifying agent neutralizer, the skin care formulation will typically include one or more agents selected from emollients, sterols or sterol derivatives, natural fats or oils, solidifying agents, viscosity enhancers, rheology modifiers, and combinations thereof. For example, the formulations of the invention may include from about 1% to about 95% by weight of one or more emollients; from about 0.1% to about 10% by weight of one or more sterols or sterol derivatives; from about 0.1% to about 95% by weight of one or more natural fats or oils; from about 5% to about 95% by weight of one or more solidifying agents; and, from about 0.1% to about 25% by weight of one or more viscosity enhancers. The formulation may include other ingredients as well. Ranges are used to describe the relative amounts of components in the formulations of the invention as well as to describe the relative physical properties of the compositions. These ranges are illustrative and one of ordinary skill in the art will recognize that the nature of the formulation will dictate the various levels of components that must be used to achieve the intended benefit for the skin barrier. The levels can be determined by routine experimentation in view of the disclosure provided herein.

As stated above, the formulations of the invention can include emollients, which are active ingredients that typically softens, soothes, supples, coats, lubricates and/or moisturizes the skin. Generally, emollients accomplish several of these objectives simultaneously. Typically, emollients suitable for use in the formulations described herein are fluids at room temperature such that they impart a soft, lubricious lotion-like feel upon use. Suitable emollients that can be incorporated into the formulations include oils such as petrolatum based oils, petrolatum, vegetable based oils, mineral oils, natural or synthetic oils, alkyl dimethicones, alkyl methicones, alkyldimethicone copolyols, phenyl silicones, alkyl trimethylsilanes, dimethicone, lanolin and its derivatives, fatty esters, glycerol esters and derivatives, propylene glycol esters and derivatives, alkoxylated carboxylic acids, alkoxylated alcohols, fatty alcohols, and combinations thereof. The esters can be selected from cetyl palmitate, stearyl palmitate, cetyl stearate, isopropyl laurate, isopropyl myristate, isopropyl palmitate, and combinations thereof. The fatty alcohols include octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients.

To provide improved stability and transfer to the skin of the wearer, the formulations may desirably include one or more emollient in an amount of from about 1% to about 95% by weight, more desirably from about 20% to about 75% by weight, and even more desirably from about 40% to about 60% by weight of the formulation. Formulations that include an amount of emollient greater than the recited amounts tend to have lower viscosities that undesirably lead to migration of the formulation. Whereas, formulations that include an amount of emollient less than the recited amounts tend to provide less transfer to the wearer's skin.

The formulations can also include sterols and sterol derivatives that act to provide natural skin barrier enhancement and skin barrier recovery. Sterols and sterol derivatives that can be used in the formulation can include, but are not limited to cholestol, sitosterol, stigmasterol, ergosterol, $C_{10}$-$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyidecanoate, ergocalciferol, tall oil sterol, soy sterol acetate, lanasterol, soy sterol, avocado sterols, fatty alcohols, and combinations thereof. The formulations of the invention can desirably include sterols, sterol derivatives or mixtures of both sterols and sterol derivatives in an amount of from about 0.1% to about 10% by weight, more desirably from about 0.5% to about 5% by weight, and even more desirably from about 0.8% to about 1% by weight of the formulation.

The formulations of the invention can also include natural fats and oils. As used herein, the term "natural fat or oil" is intended to include fats, oils, essential oils, essential fatty acids, non-essential fatty acids, phospholipids, and combinations thereof. These natural fats and oils can provide a source of essential and non-essential fatty acids to those found in the skin's natural barrier. Suitable natural fats or oils can include Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Grapeseed Oil, Safflower Oil, Sphingolipids, Seed Almond Oil, Tall Oil, Lauric Acid, Palmitic Acid, Stearic Acid, Linoleic Acid, Stearyl Alcohol, Lauryl Alcohol, Myristyl Alcohol, Behenyl Alcohol, Rose Hip Oil, Calendula Oil, Chamomile Oil, Eucalyptus Oil, Juniper Oil, Sandlewood Oil, Tea Tree Oil, Sunflower Oil, Soybean Oil, and combinations thereof.

In order to assist in replenishing skin barrier enhancing agents, the formulations of the invention may desirably include fats and oils in an amount of from about 0.1% to about 95% by weight, more desirably from about 5% to about 75% by weight, and even more desirably from about 10% to about 50% by weight of the formulation.

The solidifying agents primarily function to solidify the formulation so that the formulation is a solid at room temperature and has a penetration hardness of at least 5 mm and a melting point of at least 32° C. The solidifying agent also provides a tackiness to the formulation that improves the transfer to the skin of the wearer. Depending on the solidifying agent selected, the solidifying agent can also modify the mode of transfer so that the formulation tends to fracture or flake off instead of actually rubbing off onto the skin of the wearer which can lead to improved transfer to the skin. The solidifying agent may further function as an emollient, occlusive agent, moisturizer, barrier enhancer, and combinations thereof. The solidifying agents may include waxes as well as compounds that perform functionally as waxes.

The solidifying agents can be selected from alkyl siloxanes, polymers, hydrogenated vegetable oils having a melting point of 35° C. or greater and fatty acid esters with a melting point of 35° C. or greater. Additionally, the solidifying agents can be selected from animal, vegetable and mineral waxes and alkyl silicones. Examples of solidifying agents include, but are not limited to, alkyl trimethylsilanes, beeswax, $C_{24}$-$C_{28}$ alkyl dimethicone, $C_{30}$ alkyl dimethicone, cetyl methicone, stearyl methicone, cetyl dimethicone, stearyl dimethicone, cerotyl dimethicone, candelilla wax, carnauba, cerasin, hydrogenated microcrystalline wax, jojoba wax, microcrystalline wax, lanolin wax, ozokerite, paraffin, spermaceti wax, cetyl esters, behenyl behenate, $C_{20}$-$C_{40}$ alkyl behenate, $C_{12}$-$C_{15}$ lactate, cetyl palmitate, stearyl palmitate, isosteryl behenate, lauryl behenate, stearyl benzoate, behenyl isostearate, cetyl myristate, cetyl octanote, cetyl oleate, cetyl ricinoleate, cetyl stearate, decyl oleate, diCl$_2$-$C_{15}$ alkyl fumerate, dibehenyl fumerate, myristyl lactate, myristyl lignocerate, myristyl myristate, myristyl stearate, lauryl stearate, octyldodecyl stearate, octyldodecyl stearoyl stearate, olelyl arachidate, oleyl stearate, tridecyl behenate, tridecyl stearate, tridecyl stearoyl stearate, pentaerythrityl tetrabehenate, pentaerythrityl hydrogenated rosinate, pentaerythrityl distearate, pentaerythrityl tetraabeite, pentaerythrityl tetracocoate, pentaerythrityl tetraperlargonate, pentaerythrityl tetrastearate, theylene vinyl acetate, polyethylene, hydrogenated vegetable oil, hydrogenated squalene, hydrogenated coconut oil, hydrogenated jojoba oil, hydrogenated palm oil, hydrogenated palm kernel oil, hydrogenated olive oil, polyamides, metal stearates and other metal soaps, $C_{30}$-$C_{60}$ fatty alcohols, $C_{20+}$ fatty acids, polypropylene, polystyrene, polybutane, polybutylene terephthalate, polydipentane, zinc stearate, and combinations thereof.

To provide improved transfer to the skin of the wearer, the formulation may desirably include one or more solidifying agents in an amount of from about 5% to about 95% by weight, more desirably from about 25% to about 75% by weight, and even more desirably from about 30% to about 50% by weight of the formulation. Compositions that include an amount of solidifying agent less than the recited amounts tend to be too soft and may have lower viscosities that may undesirably lead to migration of the composition away from bodyfacing surfaces of the absorbent article, thus diminishing transfer to the wearer's skin. Whereas, formulations that include an amount of solidifying agent greater than the recited amounts tend to provide less transfer to the wearer's skin.

One or more viscosity enhancers may be added to the formulation to increase the viscosity, to help stabilize the formulation on the bodyfacing surface of the bodyside liner and, thereby, to reduce migration and improve transfer to the skin. Suitable viscosity enhancers include polyolefin resins, lipophilic/oil thickeners, ethylene/vinyl acetate copolymers, polyethylene, silica, silica silylate, silica methyl silylate, colloidal silicone dioxide, cetyl hydroxy ethyl cellulose, other organically modified celluloses, PVP/decane copolymer, PVM/MA decadiene crosspolymer, PVP/eicosene copolymer, PVP/hexadecane copolymer, and combinations thereof.

To provide the improved transfer to the skin of the wearer, the formulation may desirably include one or more viscosity enhancers in an amount of from about 0.1% to about 25% by weight, more desirably from about 3% to about 20% by weight, and even more desirably from about 5% to about 10% by weight of the formulation.

In addition to one or more viscosity enhancers, the formulations of the invention may also include one or more rheology modifiers. Rheology modifiers are compounds that increase the viscosity of the formulations at lower temperatures as well as process temperatures. Rheology modifiers are also compounds that provide "structure" to the formulations to prevent separation of insoluble and partially soluble components. By increasing the viscosity at process temperatures, the rheology modifiers will increase the viscosity above 200 centipoise. However, the rheology modifiers are thixotropic in behavior and, therefore, their viscosity decreases as shear and pressure increases. Consequently, when the rheology modifiers are used in the formulations of the invention, they maintain the suspension of insoluble and partially soluble components. This capability can be particularly important if, during processing, the formulation must be left stagnant in process lines and hoses. In addition to stabilizing the suspension of insoluble and partially soluble components, the rheology modifiers of the invention also help to stabilize the formulations on the bodyfacing surface of the bodyside liner or other materials to which the formulations are applied. Examples of suitable rheology modifiers include silica, silica silylate, silica methyl silylate, quaternary starch compounds, and combinations thereof. The formulations of the invention can suitably include one or more rheology modifiers in an amount of from about 0.5% to about 5% percent by weight of the formulation.

In order to better enhance the benefits to the wearer, additional ingredients can optionally be included in the formulations of the present invention. For example, the formulations can optionally comprise humectants, preservatives, antimicrobial actives, antifungal actives, antiseptic actives, antioxidants, astringents, biological actives, colorants, deodorants, fragrances, lubricants, natural moisturizing agents, skin conditioning agents, skin protectants, solvents, solubilizing agents, suspending agents, wetting agents, and combinations thereof.

In one embodiment of the present invention, the skin care formulation, or one or more components of the skin care formulation such as the bodily exudate modifying agent neutralizer, may be encapsulated in a shell material prior to being introduced onto the bodyside liner. When the bodily exudate modifying agents contact the bodily extrudate such as feces or menses, the capsules dissolve, disintegrate, or otherwise lose their integrity and break open to release the formulation or component(s). As discussed more fully above, the release of the formulation or components will neutralize or inhibit the action of the bodily exudate modifying agents. Suitable microencapsulation shell materials include cellulose-based polymeric materials (e.g., ethyl cellulose), carbohydrate-based materials (e.g., cationic starches and sugars), polyglycolic acid, polylactic acid, and lactic acid-based aliphatic polyesters, and materials derived therefrom (e.g., dextrins and cyclodextrins) as well as other materials compatible with human tissues.

The microencapsulation shell thickness may vary depending upon the skin care formulation utilized, and is generally manufactured to allow the encapsulated formulation or component to be covered by a thin layer of encapsulation material, which may be a monolayer or thicker laminate layer, or may be a composite layer. The microencapsulation layer should be thick enough to resist cracking or breaking of the shell during handling or shipping of the product. The microencapsulation layer should be constructed such that humidity from atmospheric conditions during storage, shipment, or wear will not cause a breakdown of the microencapsulation layer and result in a release of the formulation or component.

Microencapsulated formulations or components applied directly to the absorbent articles should be of a size such that the user cannot feel the encapsulated shell on the skin during use. Typically, the capsules have a diameter of no more than about 25 micrometers, and desirably no more than about 10 micrometers. At these sizes, there is no "gritty" or "scratchy" feeling when the formulation contacts the skin.

The viscosity of the skin care formulation must be such that the formulation is stabilized on the bodyfacing surface of the bodyside liner and, thereby, has reduced migration into the interior of the absorbent article and improved transfer to the skin. As such, the skin care formulations of the present invention typically have a viscosity of from about 10 to about 10,000 centipoise as measured at a temperature of 60° C. At 55° C., the formulations have a viscosity of from about 200 to about 100,000 centipoise.

In another embodiment of the present invention, as an alternative or in addition to using a bodily exudate modifying agent, the viscosity of bodily exudates, such as feces and menses, can be reduced by liquification of the bodily exudate. Typically, bodily exudates can be liquefied by adding water that is microencapsulated in the absorbent article. Like the bodily exudate modifying agents above, the reduction in the viscosity of the exudates will allow for enhanced absorption of the exudates into the absorbent article and away from the skin of the wearer. Suitably, the microencapsulated water reduces the viscosity of the bodily exudate by at least about 5%, more suitably, at least about 25%.

In view of the above, it will be seen that the several objects of the invention are achieved and other advantageous results obtained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. An absorbent article comprising an absorbent body, a bodyside liner, a bodily exudate modifying agent, and a skin care formulation, the bodily exudate modifying agent being an enzyme and being capable of reducing the viscosity of bodily exudates upon contact therewith, and the skin care formulation comprising a bodily exudate modifying agent neutralizer.

2. The absorbent article as set forth in claim 1 wherein the bodily exudate modifying agent is encapsulated in a shell material.

3. The absorbent article as set forth in claim 2 wherein the shell material is selected from the group consisting of cellulose-based polymeric materials, lactic acid-based aliphatic polyesters, carbohydrate-based materials, and materials derived therefrom.

4. The absorbent article as set forth in claim 1 wherein the enzyme is selected from the group consisting of amylase, lysozyme, zymolyase, celulase, protease, lipase, urease, elastase, carbohydrase, cathepsin G, myeloperoxidase, and cytolysins.

5. The absorbent article as set forth in claim 1 wherein the bodily exudate modifying agent neutralizer is an enzyme inhibitor.

6. The absorbent article as set forth in claim 5 wherein the enzyme inhibitor is selected from the group consisting of a protease inhibitor, a lipase inhibitor, an elastase inhibitor, a urease inhibitor, an amylase inhibitor, and combinations thereof.

7. The absorbent article as set forth in claim 5 wherein the enzyme inhibitor is selected from the group consisting of soybean trypsin inhibitor, lima bean protease inhibitor, corn protease inhibitor, Bowman-Birk inhibitor, pancreatic trypsin inhibitor, ovomucoids, chymostatin, leupeptin and its analogs, bestatin and its analogs, antipain, antithrombin III, hirudin, cystatin, $\alpha_2$-macroglobulin, $\alpha_1$-antitrypsin, pepstatin and its analogs, TLCK, TPCK, tranexamic acid and its salts, glycyrrhizic acid and its salts, stearylglycyrrhetinate, 18-β-glycyrrhetinic acid and its salts, colloidal oat extracts, elhibin, 4-(2-aminoethyl)-benzenesulfonylfluoride HCl, quercetin, phytic acid and its salts, ethylenediamine tetraacetic acid (EDTA) and its salts, hexamidine and its salts, pentamideine and its salts, benzamidine and its salts and derivatives, p-aminobenzamidine and its salts and derivatives, guanidinobenzoic acid and its salts and derivatives, alkyl hydroxamic acid and its salts and derivatives, phosporamidate and its derivatives, water soluble salts of metals, zinc salts of both saturated and unsaturated monocarboxylic acids, glycerol triesters of fatty acids, block copolymers of propylene oxide and ethylene oxide, chlorhexidine, cholestyramine, acarbose, voglibose, miglitol, emiglitate, camiglibose, pradimicin Q, salbostatin, tendamistat, trestatins, inhibitors derived from plants, such as from wheat, rice, maize, barley, and other cereal grains, beans, and seaweed, tetrahydrolipstatin, lipstatin, valilactone, esterastin, ebelactone A and B, 1,6-di(O-carbamoyl)cyclohexanone oxime)hexane, and combinations thereof.

8. The absorbent article as set forth in claim 1 wherein the bodily exudate modifying agent neutralizer is a skin irritant sequestering agent.

9. The absorbent article as set forth in claim 8 wherein the sequestering agent is a clay.

10. The absorbent article as set forth in claim 9 wherein the clay is selected from the group consisting of bentonite, laponite, montmorillonite, beidelite, hectorite, saponite, stevensite, and combinations thereof.

11. The absorbent article as set forth in claim 8 wherein the sequestering agent is selected from the group consisting of silica, titanium dioxide, hydroxyapatite, alumina, ion-exchange resin, and combinations thereof.

12. The absorbent article as set forth in claim 1 wherein the bodily exudate modifying agent neutralizer is an oxidizing agent.

13. The absorbent article as set forth in claim 12 wherein the oxidizing agent is selected from citric acid, malic acid, alphahydroxy acid, hydrogen peroxide, and peroxide.

14. The absorbent article as set forth in claim 1 wherein the bodily exudate modifying agent neutralizer is a binding protein.

15. The absorbent article as set forth in claim 14 wherein the binding protein is selected from the group consisting of serum albumin, histone proteins, plant proteins, animal proteins, fish proteins, yeast extract, algal proteins, and bacterial proteins.

16. The absorbent article as set forth in claim 1 wherein the bodily exudate modifying agent neutralizer is a zwitterion.

17. The absorbent article as set forth in claim 16 wherein the zwitterion is an amino acid.

18. The absorbent article as set forth in claim 1 wherein the bodily exudate modifying agent neutralizer is present in the skin care formulation in an amount of from about 0.1% by weight of the formulation to about 10% by weight of the formulation.

19. The absorbent article as set forth in claim 1 wherein the skin care formulation further comprises a component selected from the group consisting of emollients, sterol or sterol derivatives, natural fats or oils, solidifying agents, viscosity enhancers, and combinations thereof.

20. The absorbent article as set forth in claim 1 wherein the skin care formulation further comprises an optional ingredient selected from the group consisting of humectants, preservatives, antimicrobial actives, antifungal actives, antiseptic actives, antioxidants, astringents, biological actives, colorants, deodorants, fragrances, lubricants, natural moisturizing agents, skin conditioning agents, skin protectants, solvents, solubilizing agents, suspending agents, wetting agents, and combinations thereof.

21. The absorbent article as set forth in claim 1 wherein the skin care formulation is microencapsulated in a shell material.

22. The absorbent article as set forth in claim 21 wherein the shell material comprises a material selected from the group consisting of cellulose-based polymeric materials, carbohydrate-based materials, polyglycolic acid, polylactic acid, lactic acid-based aliphatic polyesters, and materials derived therefrom.

23. The absorbent article as set forth in claim 1 wherein the bodily exudate modifying agent neutralizer is microencapsulated.

24. The absorbent article as set forth in claim 23 wherein the shell material comprises a material selected from the group consisting of cellulose-based polymeric materials, carbohydrate-based materials, polyglycolic acid, polylactic acid, lactic acid-based aliphatic polyesters, and materials derived therefrom.

25. The absorbent article as set forth in claim 1 wherein the skin care formulation has a viscosity of from about 10 to about 10,000 centipoise at a temperature of 60° C.

26. The absorbent article as set forth in claim 1 wherein the bodily exudate modifying agent and the skin care formulation are located on the bodyside liner of the absorbent article.

27. The absorbent article as set forth in claim 1 wherein the bodily exudate modifying agent is located in the absorbent body of the absorbent article and the skin care formulation is located on the bodyside liner of the absorbent article.

28. The absorbent article as set forth in claim 1 wherein the absorbent article is selected from the group consisting of diapers, training pants, adult incontinence garments, and feminine napkins.

29. An absorbent article comprising an absorbent body, a bodyside liner, microencapsulated water, a bodily exudate modifying agent, and a skin care formulation, the bodily exudate modifying agent being an enzyme and being capable of reducing the viscosity of bodily exudates upon contact therewith, and the skin care formulation comprising a bodily exudate modifying agent neutralizer.

30. The absorbent article as set forth in claim 29 wherein the water is encapsulated in a shell material comprising a material selected from the group consisting of cellulose-based polymeric materials, lactic acid-based aliphatic polyesters, carbohydrate-based materials, and materials derived therefrom.

31. The absorbent article as set forth in claim 29 wherein the bodily exudate modifying agent is encapsulated in a shell material.

32. The absorbent article as set forth in claim 29 wherein the enzyme is selected from the group consisting of amylase, lysozyme, zymolyase, celulase, protease, lipase, urease, elastase, carbohydrase, cathepsin G, myeloperoxidase, and cytolysins.

33. The absorbent article as set forth in claim 29 wherein the bodily exudate modifying agent neutralizer is an enzyme inhibitor.

34. The absorbent article as set forth in claim 33 wherein the enzyme inhibitor is selected from the group consisting of a protease inhibitor, a lipase inhibitor, an elastase inhibitor, a urease inhibitor, an amylase inhibitor, and combinations thereof.

35. The absorbent article as set forth in claim 34 wherein the enzyme inhibitor is selected from the group consisting of soybean trypsin inhibitor, lima bean protease inhibitor, corn protease inhibitor, Bowman-Birk inhibitor, pancreatic trypsin inhibitor, ovomucoids, chymostatin, leupeptin and its analogs, bestatin and its analogs, antipain, antithrombin III, hirudin, cystatin, $\alpha_2$-macroglobulin, $\alpha_1$-antitrypsin, pepstatin and its analogs, TLCK, TPCK, tranexamic acid and its salts, glycyrrhizic acid and its salts, stearylglycyrrhetinate, 18-$\beta$-glycyrrhetinic acid and its salts, colloidal oat extracts, elhibin, 4-(2-aminoethyl)-benzenesulfonylfluoride HCl, quercetin, phytic acid and its salts, ethylenediamine tetraacetic acid (EDTA) and its salts, hexamidine and its salts, pentamideine and its salts, benzamidine and its salts and derivatives, p-aminobenzamidine and its salts and derivatives, guanidinobenzoic acid and its salts and derivatives, alkyl hydroxamic acid and its salts and derivatives, phosporamidate and its derivatives, water soluble salts of metals, zinc salts of both saturated and unsaturated monocarboxylic acids, glycerol triesters of fatty acids, block copolymers of propylene oxide and ethylene oxide, chlorhexidine, cholestyramine, acarbose, voglibose, miglitol, emiglitate, camiglibose, pradimicin Q, salbostatin, tendamistat, trestatins, inhibitors derived from plants, such as from wheat, rice, maize, barley, and other cereal grains, beans, and seaweed, tetrahydrolipstatin, lipstatin, valilactone, esterastin, ebelactone A and B, 1,6-di(O-carbamoyl)cyclohexanone oxime)hexane, and combinations thereof.

36. The absorbent article as set forth in claim 29 wherein the bodily exudate modifying agent neutralizer is a skin irritant sequestering agent.

37. The absorbent article as set forth in claim 36 wherein the sequestering agent is a clay.

38. The absorbent article as set forth in claim 37 wherein the clay is selected from the group consisting of bentonite, laponite, montmorillonite, beidelite, hectorite, saponite, stevensite, and combinations thereof.

39. The absorbent article as set forth in claim 36 wherein the sequestering agent is selected from the group consisting of silica, titanium dioxide, hydroxyapatite, alumina, ion-exchange resin, and combinations thereof.

40. The absorbent article as set forth in claim 29 wherein the bodily exudate modifying agent neutralizer is an oxidizing agent.

41. The absorbent article as set forth in claim 40 wherein the oxidizing agent is selected from citric acid, malic acid, alphahydroxy acid, hydrogen peroxide, and peroxide.

42. The absorbent article as set forth in claim 29 wherein the bodily exudate modifying agent neutralizer is a binding protein.

43. The absorbent article as set forth in claim 42 wherein the binding protein is selected from the group consisting of serum albumin, histone proteins, plant proteins, animal proteins, fish proteins, yeast extract, algal proteins, and bacterial proteins.

44. The absorbent article as set forth in claim 29 wherein the bodily exudate modifying agent neutralizer is a zwitterion.

45. The absorbent article as set forth in claim 44 wherein the zwitterion is an amino acid.

46. The absorbent article as set forth in claim 29 wherein the bodily exudate modifying agent neutralizer is present in the skin care formulation in an amount of from about 0.1% by weight of the formulation to about 10% by weight of the formulation.

47. The absorbent article as set forth in claim 29 wherein the skin care formulation further comprises a component selected from the group consisting of emollients, sterol or sterol derivatives, natural fats or oils, solidifying agents, viscosity enhancers, and combinations thereof.

48. The absorbent article as set forth in claim 29 wherein the skin care formulation further comprises an optional ingredient selected from the group consisting of humectants, preservatives, antimicrobial actives, antifungal actives, antiseptic actives, antioxidants, astringents, biological actives, colorants, deodorants, fragrances, lubricants, natural moisturizing agents, skin conditioning agents, skin protectants, solvents, solubilizing agents, suspending agents, wetting agents, and combinations thereof.

49. The absorbent article as set forth in claim 29 wherein the skin care formulation is microencapsulated in a shell material.

50. The absorbent article as set forth in claim 49 wherein the shell material comprises a material selected from the group consisting of cellulose-based polymeric materials, carbohydrate-based materials, polyglycolic acid, polylactic acid, lactic acid-based aliphatic polyesters, and materials derived therefrom.

51. The absorbent article as set forth in claim 29 wherein the skin care formulation has a viscosity of from about 10 to about 10,000 centipoise at a temperature of 60° C.

52. The absorbent article as set forth in claim 29 wherein the microencapsulated water, the bodily exudate modifying agent, and the skin care formulation are located on the bodyside liner of the absorbent article.

53. The absorbent article as set forth in claim 29 wherein the microencapsulated water and the bodily exudate modifying agent are located in the absorbent body of the absorbent article and the skin care formulation is located on the bodyside liner of the absorbent article.

54. The absorbent article as set forth in claim 29 wherein the absorbent article is selected from the group consisting of diapers, training pants, adult incontinence garments, and feminine napkins.

* * * * *